United States Patent [19]

Sitnik

[11] Patent Number: 4,870,962
[45] Date of Patent: Oct. 3, 1989

[54] DISPOSABLE SELF-INFLATING MANUAL RESUSCITATOR BAG

[76] Inventor: Lee Sitnik, 200 Kirkstone Rd., Irmo, S.C. 29063

[21] Appl. No.: 96,464

[22] Filed: Sep. 14, 1987

[51] Int. Cl.$^4$ ................................................ A62B 7/00
[52] U.S. Cl. ............................ 128/205.13; 128/205.24
[58] Field of Search .................... 92/34, 42; 417/472; 128/203.28, 204.28, 205.13, 205.17, 28, 727, 728

[56] References Cited

U.S. PATENT DOCUMENTS

| | | | |
|---|---|---|---|
| 1,197,232 | 9/1916 | Pierpont . | |
| 2,609,000 | 9/1952 | Moabray | 92/34 |
| 2,931,357 | 4/1966 | Arborelius et al. | 128/204.28 |
| 3,120,192 | 2/1964 | Winchell | 417/472 |
| 3,196,866 | 7/1965 | Adams . | |
| 3,495,502 | 2/1970 | Bousso | 92/47 |
| 3,606,623 | 9/1971 | Aymar | 417/472 |
| 3,882,860 | 5/1978 | Frimberger | 128/205.13 |
| 4,187,845 | 2/1980 | Dror | 128/205.13 |
| 4,336,747 | 6/1982 | Tohy et al. | 92/47 |
| 4,441,506 | 4/1984 | McCombs et al. | 128/728 |
| 4,532,923 | 8/1985 | Flynn . | |
| 4,549,015 | 9/1982 | Alferness | 128/205.17 |

*Primary Examiner*—Edward M. Coven
*Assistant Examiner*—K. M. Reichle
*Attorney, Agent, or Firm*—F. Rhett Brockington

[57] ABSTRACT

A manually actuated, self-distending, self-inflating resuscitator bag that is substantially shaped like a pleated, handleless bellows where the pleats act like a spring following compression to rapidly re-inflate the bag to its fully recovered state, and that the flat sides of the bellows enable the operator to easily pump the bag with one hand or a knee as there is no tendency to roll away during the compression cycle.

10 Claims, 1 Drawing Sheet

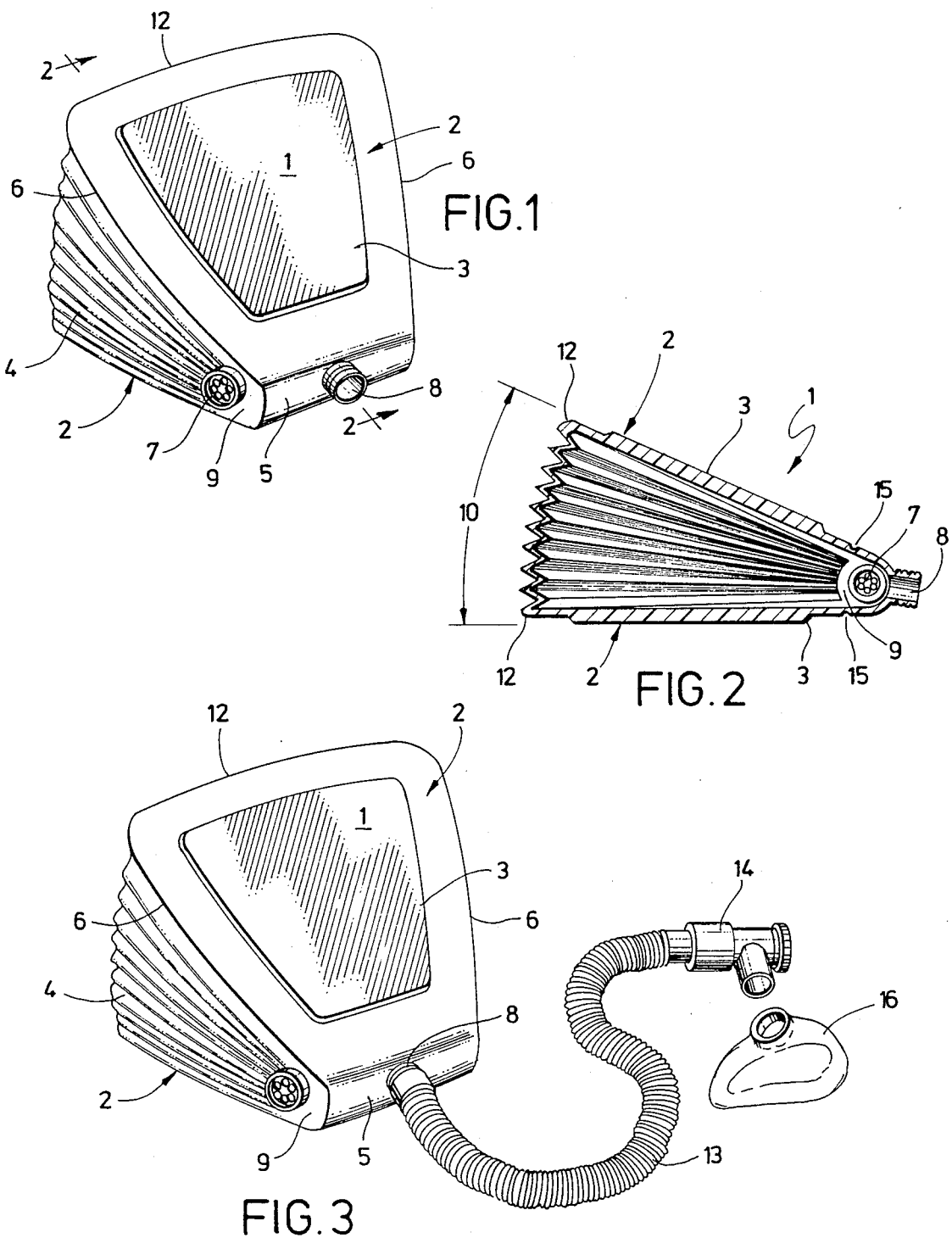

DISPOSABLE SELF-INFLATING MANUAL RESUSCITATOR BAG

FIELD OF THE INVENTION

This invention relates generally to apparatus for affecting cardiopulmonary resuscitation, when breathing has been halted or impaired by immersion or other suffocating circumstances, and more specifically to apparatus for reestablishing breathing, where such apparatus are portable, manuallya ctuated and designed for emergency use.

BACKGROUND OF THE INVENTION AND PRIOR ACT

Mechanical, cardiopulmanary resuscitators have been reported in the patent literature for over seventy years. In 1916, Pierpoint No. 1,197,232 disclosed an apparatus in which pressurized air, generated by a hand held bellows, is forced through a two way inhalation-exhalation valve, through a tube leading to a face mask and into the trahea and lungs of the distressed individual. Upon exhalation, air exhausts in the reverse direction through the two way valve. Pierpont's invention has served as a benchmark for manaul resuscitators for over the years. While refinements have been made, the basic precepts of Pierpoint's invention have remained largely intact.

Exemplary of such a refinement was Adam's Pat. No. 3,196,866 resuscitator, which recognized the need for a two way valve that would normally stay open, therein obviating the need for repetitive pumping of the bellows once breathing was restarted. Additionally, the hand operated bellows was replaced with a self-distending football shaped elastic bag that was lightweight, portable and reportedly required only one hand to compress.

Flynn Pat. No. 4,532,923 described an improved resuscitator bag that has a ribbed football shape. He contends in his patent that thin walled bags, those which can be compressed with one hand, do not recover to their normal shape fast enough especially in emergency situations, and this precipitates anxiety in the operators as they find it very difficult to jude how much air has been forced into the distressed individual's lungs. As a consequence of this uncertainty the operators often over compensate, which results in a tendency to over pressurize the lungs. Flynn proposed that a thicker, ribbed, rapidily self-inflating bag will aleviate most of those concerns, and the operator will be less likely to over compensate.

The applicant's own experience reinforces the necessity for a fast recovering bag, however, this feature has to be tempered with the recognition that the operator's hands will quickly tire compressing a stiff bag. As a consequence the operator will become less effective at rendering other emergency procedures requiring manual dexterity, such as ensuring that the throat passage is clear, holding up the jaw and adjusting the face mask. Under certain circumstances there is the need for the freedom to be able to use both hands.

Additionally, with increasing costs for skilled medical labor and a growing concern about the accidental transmission of virulent contagious diseases, more and more respiractory technologists are recognizing the benefits of disposable equipment. There is no chance of cross-contamination and lengthy cleaning procedures are eliminated.

SUMMARY OF THE INVENTION

An object of the instant invention is to provide a self-inflating, self-distending bellows shaped resuscitator bag which has at least one air and/or oxygen intake valve and an air exhaust port. A bellows shaped bag is preferred because in contrast to a football or other spherically shaped bag, as the bellows is compressed a linear quantity of air is expelled from the inner chamber of the bellows as the walls are collapsed; therein making it much easier for the operator to estimate how much air has been forced into the receipient's lungs. Another advantage of a bellows shaped bag is that one edge can be hinged, thereby enabling a mechanical advantage to be incorpoated in the design. The mechanical advantage enables an operator to compress, with one hand, a relatively stiff bag without becoming physically fatigued. A further advantage of a bellows shaped bag is that its flat sides eliminate any tendency to roll away while being compressed, and this enables an operator to compress it under his arm or knee, therein freeing both his hands for performing other tasks.

A further object of the invention is that the bag can be fabricated using interated single piece construction, being molded from a thermoplastic or other suitable material. One piece construction results in lower manufacturing costs per unit, and this should bring the bag down into a price range as to render it disposable.

A further object of the invention is that the bag is constructed of materials which are moldable and are very resilient, such as a polyvinyl plastic or a polyurethane. The plates of the bellows are thick enough, in comparison to the pleats of the compressible walls, so as to act relatively rigid. Reinforcing ribs are added as required. The pleats are constructed sufficiently thick such that the bellows totally recovers to full inflation in less than four seconds after being completely compressed.

A further object of the invention is that the bag can be connected via a section of flexible tubing to a two way inhalation-exhalation valve, where the connectingn tubing enables the operator to move the resuscitator bag away from the face of the distresed individual, enabling the operator to have a nearly unobstructed view of the patient.

A further object of the invention is that the bag can be connected to a regulated supply of oxygen (or another reservoir of oxygen) via an attachment that connects the air intake valve to the oxygen supply.

A final object of the invention is that the bag is compatible with a full line of resuscitation equipment (i.e. endotracheal and tracheostomy tubes) that is currently commercially available, and the instant invention can readily be substituted for the conventional football shaped resuscitator bag.

BRIEF DESCRIPTION OF THE DRAWINGS

FIG. 1 is a perspective view of the bellows shaped resuscitator bag.

FIG. 2 is a longitudinal section view of the bag as shown in FIG. 1 taken along the plane as indicated by sectional line 2—2.

FIG. 3 is a perspective view of the resuscitator fitted with auxillar resuscitation gear.

DETAILED DESCRIPTION OF THE ILLUSTRATED EMBODIMENT

The bag 1 is approximately two liters in volume and is shaped, as shown in FIG. 1, like a pleated, handleless bellows. The bag is formed using a molding process from polyethylene, and therefore except for a few working elements, it is comprised substantially of a single polymeric material. The bag is fitted with an air (and/or oxygen) intake valve 7 through which air is drawn during its self-inflation portion of the pump cycle. There is an air (and/or oxygen) outlet 8 through which air is expelled from the inner chamber of the bellows during compression. The air inlet valve 7 is a one way valve and it is closed during compression.

The angle 10 formed by the plates 2 of the bellows is approximately 40 degrees when the bag is fully distended. The plates 2 and the lateral collapsible pleated wall 4 are hinged at the anterior portion of the bellows to a stiffened, semi-cylindrical shaped element or binding 5. The binding's walls are contiguous with the anterior most portions of the plates and both sides of the lateral pleated walls.

The air outlet 8, an orifice having a rigid, ridged cylindrical neck, is centrally located in the binding 5. The air intake valve 7, which is also an orifice having a rigid ridged cylindrical neck which in addition is fitted with a one-way valve is located in either of the lateral walls 7 of the binding. The lateral collapsible walls 4 and the posterior collapsible wall 11 shown in FIG. 2 are contiguous with the remaining edges of the plates 2. The depth of pleating of the lateral walls 4 tapers as you move anteriorly. The pleating has an essentially radial distribution about the lateral walls 9 of the binding.

FIG. 2, which is a vertical sectional view of the bag 1 taken along sectional line 2—2 in FIG. 1 particularly illustrates this distribution.

The pleated walls, 11 and 4, act under compression like a recoiling spring ot automatically restore the bag to a state of full distention (full inflation). The binding 5 will also act to restore the bellows to full distention, however during compression, the binding will tend to deform the air intake valve 7 and the air outlet 8 which could result in leaks, therefore, there is a groove 15 at the point of junction between the plate 2 and the binding 5, the groove 15 permits the plate to be folded without distorting the binding. During decompression the parptial vacuum exers a force on the two plates causing them to want to belly inward. This movement has been essentially eliminated by reinforcing the plates with a thick layer of plastic 3. The ngled orientation of the folds of the pleated lateral and posterior walls 11 and 4 prevents the thinner, relatively flexible, compressible wall from yielding either under compression or decompression.

FIG. 3 shows the resuscitator bag 1 fully configured with a flexible, corrugated, 18 inches long tube 13, a two way inhalation-exhalation valve 14 and a face mask 16. The diameter of the air intake valve and the tubing is 1½ inches. The lateral edges 6 of the bellows' plates are 8 inches long, the posterior edges 12 are 9 inches long and the binding 5 is 6 inches long.

I claim:

1. A manually actuated, self-inflating and self-distending resuscitator bag, for restoring breathing to
   a patient whose breathing process has been interrupted or impaired, where the bag, by alternating compression and inflation of the same, is utilized to generate a known, rhythmic supply of pressurized breathing gas, wherein said bag consists of:
   a normally expanded bellows;
   said bellows having a pair of substantially stiff, similar, opposing, upper and lower plates, a substantially stiff semi-cyclindrical binding, of a length equal to that of opposing peripheral side edges of said upper and lower plates, hingedly joined along the longitudinal edges thereof to the opposing peripheral side edges of said upper and lower plates, respectively, a pleated collapsible side wall, which s flexible and elastic in comparison to the plates, adjoining the remaining edges of the opposing pair of plates and the binding, a pressurizable chamber formed by the combination of the plates, binding and sidewall,
   a breathing gas intake valve thereon that opens under a slight vacuum, enabling gas to be drawn into the chamber, and closes under slight positive pressure and
   a breathing gas outlet thereon through which the gas within the chamber of the bellows is expelled;
   said bellows forming a unitary structure and composed of moldable plastic resilient material; each of said pair of opposing plates being reinforced with a thicker cross section of moldable resilient plastic material therein imparting further structural stiffness;
   said semi-cylindrical binding having walls closing opposite ends of the length thereof, respectively, which extend beyond the arc defined by the perimeter of the ends toward said pleated collapsible sidewall, said binding serving to prevent said bound edges of the plates from collapsing against one another during compressing;
   the pleats in the pleated collapsible lateral walls symmetrically radiating from the binding end walls at an angle that is a fractional component of that angle formed by the pair of opposing plates, such that as the latter angle becomes more acute, as during compression of the bag, the angle cut by the pleats becomes more acute and strained, and that this strained angle causes the pleated collapsible wall to react as a compressed spring, and exerts a countering force which serves to make the bag inherently self-distending and self-inflating;
   said breathing gas outlet consisting of an opening in said bag which fluidically communicates with said chamber and means for connecting the opening to a patient breathing gas administration means which includes an externally ridged tube connected to the opening and protruding from said bag; and
   said breathing gas intake valve consisting of an opening in said bag which fluidically communicates with said chamber, means for connecting the opening to a source of breathing gas which includes no externally ridged tube connected to the opening and protruding from said bag and one-way valve means for opening when a slight vacuum is produced within said bag during inflation of the same and sealing said opening when a slight positive pressure is produced within said bag during compression of the same.

2. The bag as claimed in claim 1 further including a hose having fastening means for connecting to the ridged tube of said breathing gas outlet at one end and means for connecting the hose to the patient at the other end.

3. The bag as claimed in claim 2, wherein said means for connecting the hose to the patient includes a face mask and two-way, inhalation-exhalation valve means connected between said other end of said hose and said face mask.

4. The bag as claimed in claim 1, wherein the moldable resilient plastic material is polyethylene.

5. The bag as claimed in claim 4, wherein the moldable resilient plastic material
  hingedly joining the edges of the plates to the binding is of smaller cross-sectional thickness than that of either the plate or the binding, therein allowing the plate to be folded during compression or inflation without distorting the binding.

6. The bag as claimed in claim 5, wherein the bag has a volume of approximately two liters.

7. The bag as claimed in claim 6, wherein said breathing gas outlet is centrally located on said binding.

8. The bag as claimed in claim 7, wherein said breathing gas intake valve is located on a end wall of the binding.

9. The bag as claimed in claim 8, wherein the angle formed between the plates is approximately 40 degrees when the bag is fully distended.

10. The bag as claimed in claim 9, where the angle formed between the plates is substantially 0 degrees when the bag is fully compressed.

* * * * *